(12) United States Patent
Trichopoulos et al.

(10) Patent No.: US 10,839,189 B2
(45) Date of Patent: Nov. 17, 2020

(54) METHODS, APPARATUSES, AND SYSTEMS FOR RADIO-FREQUENCY IMAGING SENSORS FOR ADVANCED FINGERPRINT BIOMETRICS AND MEDICAL IMAGING

(71) Applicants: Georgios Trichopoulos, Tempe, AZ (US); Panagiotis Theofanopoulos, Tempe, AZ (US)

(72) Inventors: Georgios Trichopoulos, Tempe, AZ (US); Panagiotis Theofanopoulos, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 16/309,188

(22) PCT Filed: Jun. 14, 2017

(86) PCT No.: PCT/IB2017/053548
§ 371 (c)(1),
(2) Date: Dec. 12, 2018

(87) PCT Pub. No.: WO2017/216745
PCT Pub. Date: Dec. 21, 2017

(65) Prior Publication Data
US 2019/0318146 A1    Oct. 17, 2019

Related U.S. Application Data

(60) Provisional application No. 62/349,893, filed on Jun. 14, 2016.

(51) Int. Cl.
*G06F 3/0481* (2013.01)
*G06K 9/00* (2006.01)
(Continued)

(52) U.S. Cl.
CPC .......... *G06K 9/0002* (2013.01); *A61B 5/0507* (2013.01); *A61B 5/1172* (2013.01);
(Continued)

(58) Field of Classification Search
CPC ...... G01S 13/89; G06F 3/04886; G01J 5/046; G01N 21/3581; H01M 2/0275
(Continued)

(56) References Cited

U.S. PATENT DOCUMENTS

2006/0085160 A1*   4/2006   Ouchi ................ G01N 21/3581
                                                    702/150
2007/0047678 A1    3/2007   Sibecas et al.
(Continued)

OTHER PUBLICATIONS

International Search Report and Written Opinion for International Patent Application No. PCT/IB2017/053548, dated Aug. 28, 2017, 10 pages.
(Continued)

*Primary Examiner* — Abdul-Samad A Adediran
(74) *Attorney, Agent, or Firm* — Withrow & Terranova, P.L.L.C.

(57) ABSTRACT

Methods, apparatuses, systems, and implementations of an ultra-compact RF (30 GHz-10 THz) imaging sensor topology that provides a new insight into the human skin are disclosed. The skin tissue is the largest organ in the body—both in weight and surface area—and stores valuable information that can revolutionize security biometrics and mobile health monitoring. The proposed compact sensor enables, for the first time, portable and wearable devices to perform superior biometric authentication compared to current fingerprint methods. Additionally, these devices could probe into the skin to monitor vital signs in real-time and enable mobile health monitoring.

20 Claims, 12 Drawing Sheets

(51) Int. Cl.
| | |
|---|---|
| *A61B 5/05* | (2006.01) |
| *A61B 5/1172* | (2016.01) |
| *G06T 7/00* | (2017.01) |
| *H01Q 15/24* | (2006.01) |
| *G06F 3/0488* | (2013.01) |
| *H01Q 1/36* | (2006.01) |
| *H01Q 21/06* | (2006.01) |

(52) U.S. Cl.
CPC ..... *G06F 3/04886* (2013.01); *G06K 9/00087* (2013.01); *G06T 7/0014* (2013.01); *H01Q 15/24* (2013.01); *A61B 2562/028* (2013.01); *G06T 2207/30088* (2013.01); *H01Q 1/368* (2013.01); *H01Q 21/062* (2013.01); *H01Q 21/064* (2013.01)

(58) Field of Classification Search
USPC .......... 250/338.3; 342/22; 345/174; 702/150
See application file for complete search history.

(56) References Cited

U.S. PATENT DOCUMENTS

| | | | |
|---|---|---|---|
| 2008/0030302 | A1 | 2/2008 | Franza et al. |
| 2008/0081567 | A1 | 4/2008 | Rofougaran |
| 2011/0254727 | A1 | 10/2011 | Kam et al. |
| 2012/0105267 | A1* | 5/2012 | DeLia ............... G01S 13/89 342/22 |
| 2013/0175506 | A1 | 7/2013 | Heo et al. |
| 2016/0065169 | A1* | 3/2016 | Rinaldi ............... G01J 5/046 250/338.3 |
| 2016/0179338 | A1* | 6/2016 | Miller ............... G06F 3/04886 345/174 |
| 2017/0033326 | A1* | 2/2017 | Goto ............... H01M 2/0275 |

OTHER PUBLICATIONS

International Preliminary Report on Patentability for International Patent Application No. PCT/IB2017/053548, dated Dec. 27, 2018, 10 pages.
Ali, Khaled, et al., "Photo-Induced Coplanar Waveguide RF Switch and Optical Crosstalk on High-Resistivity Silicon Trap-Rich Passivated Substrate," IEEE Transactions on Electron Devices, vol. 60, Issue 10, Oct. 2013, pp. 3478-3484.
Arora, Sunpreet, et al., "3D Fingerprint Phantoms," 22nd International Conference on Pattern Recognition, 2014, IEEE, pp. 684-689.
Auksorious, Egidijus, et al., "Fingerprint imaging from the inside of a finger with full-field optical coherence tomography," Biomedical Optics Express, vol. 6, Issue 11, Nov. 2015, 7 page.
Britnell, L., et al., "Field-Effect Tunneling Transistor Based on Vertical Graphene Heterostructures," Science, vol. 335, Feb. 2012, pp. 947-950.
Castro, Eduardo, et al., "Electronic properties of a biased graphene bilayer," Journal of Physics: Condensed Matter, vol. 22, Issue 17, Apr. 2010, 15 pages.
Cooper, Ken, et al., "Penetrating 3D Imaging at 4- and 25-m Range Using a Submillimeter-Wave Radar", IEEE Transactions on Microwave Theory and Techniques, vol. 56, Issue 12, Dec. 2008, pp. 2771-2778.
Fallahi, Arya, et al., "Design of Tunable Biperiodic Graphene Metasurfaces," Physical Review B, vol. 86, Issue 19, Oct. 2012, 9 pages.
Gomez-Diaz, J.S., et al., "Self-biased reconfigurable graphene stacks for terahertz plasmonics," Nature Communications, vol. 6, Article No. 6334, Mar. 2015, Macmillan Publishers Limited, 8 pages.
Heikenfeld, Jason, "Sweat Sensors Will Change How Wearables Track Your Health," IEEE Spectrum, Oct. 22, 2014, 8 pages.
Levy, D.M., et al., "Changes in cholinergic sweat gland activation in diabetic neuropathy identified by computerised sweatspot analysis," Diabetologia, vol. 34, Issue 11, Nov. 1991, pp. 807-812.
Mafinejad, Yasser, et al., "Impact of Carbon Material on RF MEMS Switch," 21st Iranian Conference on Electrical Engineering, May 2013, Mashhad, Iran, IEEE, 4 pages.
Milaninia, Kaveh, et al., "All graphene electromechanical switch fabricated by chemical vapor deposition," Applied Physics Letters, vol. 95, Article No. 183105, 2009, 3 pages.
Pfeiffer, Ulrich, et al., "A 0.53 THz Reconfigurable Source Module with Up to 1 mW Radiated Power for Diffuse Illumination in Terahertz Imaging Applications", IEEE Journal of Solid-State Circuits, vol. 49, Issue 12, Dec. 2014, IEEE, pp. 2938-2950.
Pickwell, E., et al., "In vivo study of human skin using pulsed terahertz radiation," Physics in Medicine and Biology, vol. 49, 2004, IOP Publishing Ltd, 1595-1607.
Ryder, et al. "Acetylcholine Sweatspot Test for Autonomic Denervation," Lancet, vol. 1, Issue 8598, Jun. 1988, pp. 1303-1305.
Taylor, Zachary, et al., "THz Medical Imaging: in vivo Hydration Sensing," IEEE Transactions on Terahertz Science and Technology, vol. 1, Issue 1, Sep. 2011, pp. 201-219.
Trichopoulous, Georgios, et al., "A Broadband Focal Plane Array Camera for Real-time THz Imaging Applications," IEEE Transactions on Antennas and Propagation, vol. 61, Issue 4, Apr. 2013, pp. 1733-1740.
Von Spiegel, Wolff, et al., "Illumination Aspects in Active Terahertz Imaging," IEEE Transactions on Microwave Theory and Techniques, vol. 58, Issue 7, Jul. 2010, pp. 2008-2013.
Tripathi, Saroj, et al., "Morphology of human sweat ducts observed by optica coherence tomography and their frequency of resonance in the terahertz frequency region," Nature, Scientific Reports, vol. 5, Article No. 9071, Mar. 2015, 7 pages.
Yarahmadi, Morteza, et al., "Subwavelength Graphene-Based Plasmonic THz Switches and Logic Gates," IEEE Transactions on Terahertz Science and Technology, vol. 5, Issue 5, Sep. 2015, 7 pages.
Zhenwei, Xie, et al., "Spacial Terahertz Modulator," Scientific Reports, vol. 3, Article No. 3347, Nov. 2013, 4 pages.

\* cited by examiner

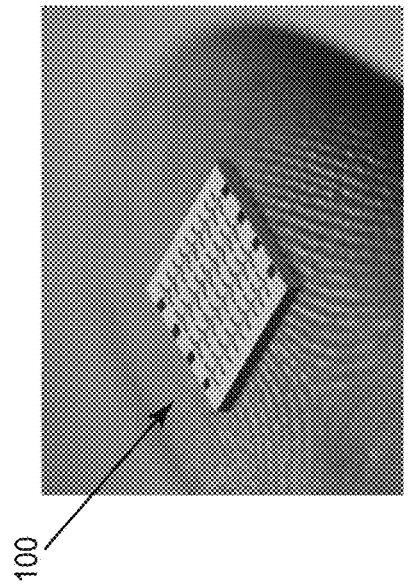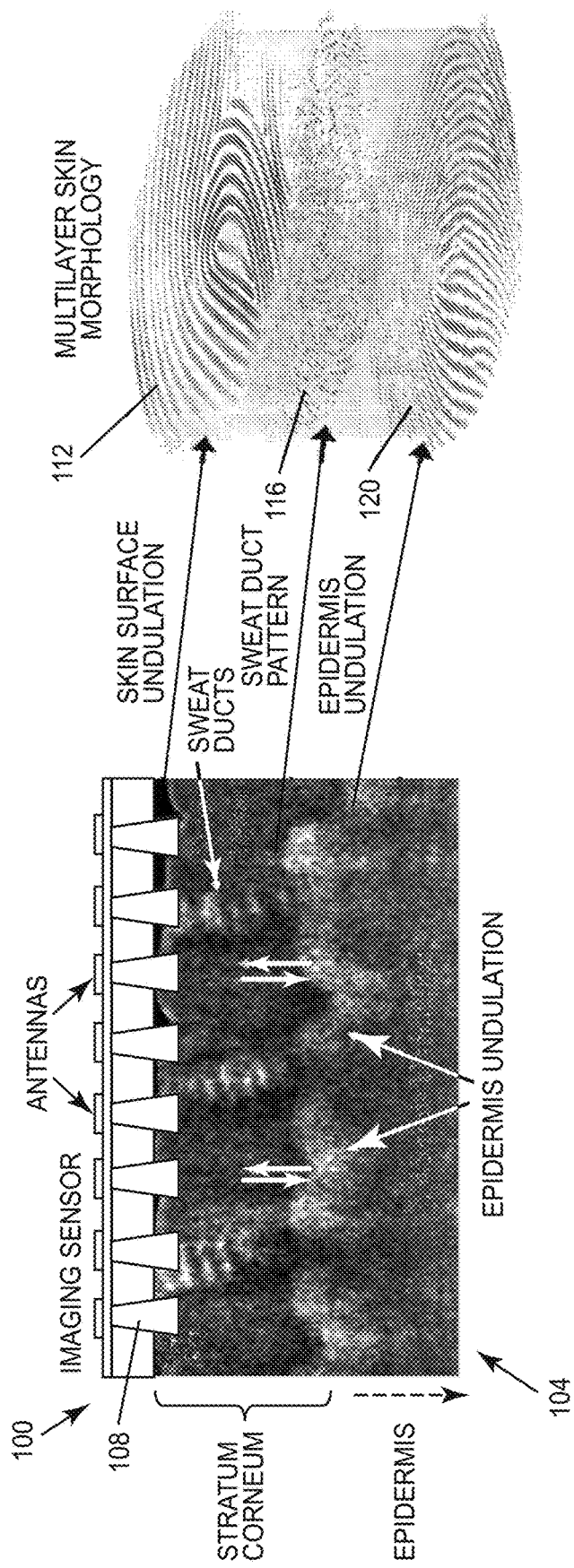

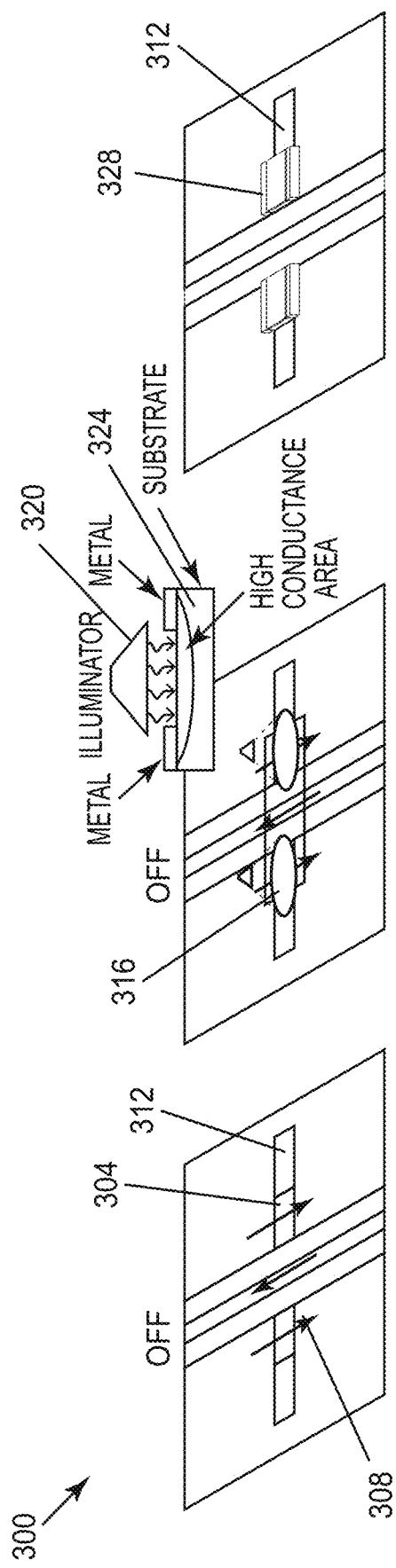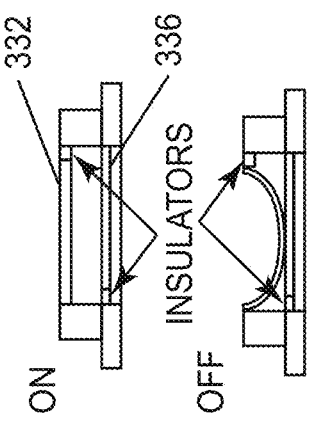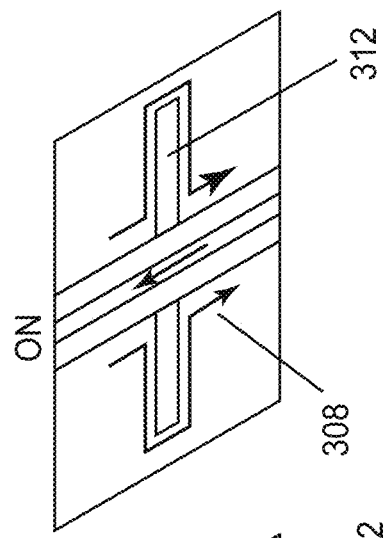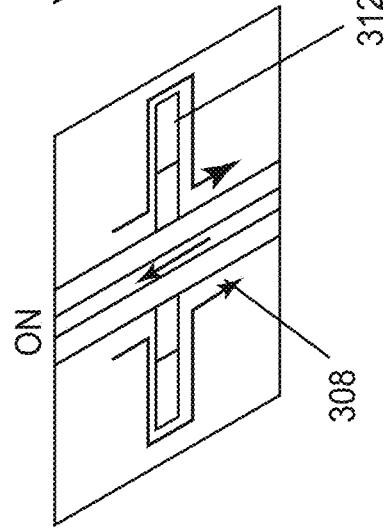
FIG. 3A  FIG. 3B  FIG. 3C  FIG. 3D  FIG. 3E  FIG. 3F

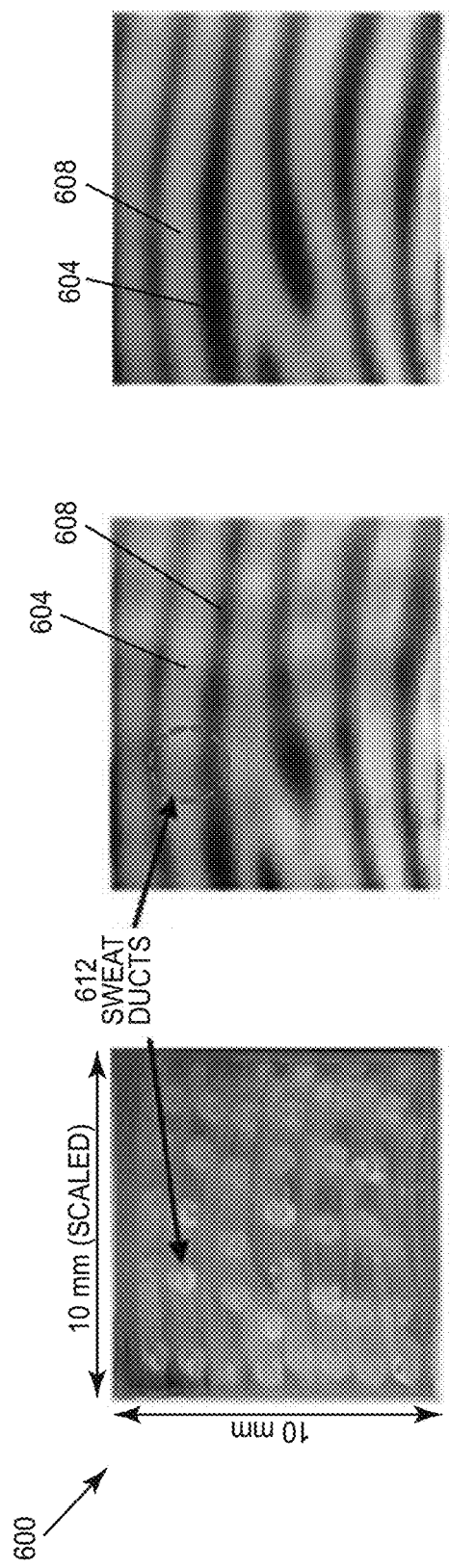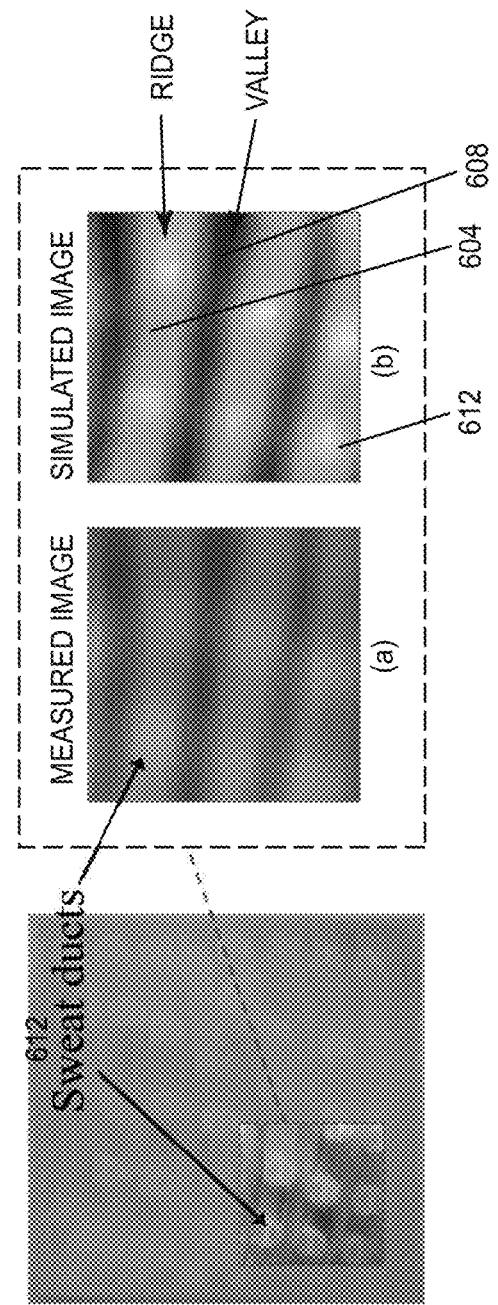
FIG. 6A, FIG. 6B, FIG. 6C, FIG. 6D

METHODS, APPARATUSES, AND SYSTEMS FOR RADIO-FREQUENCY IMAGING SENSORS FOR ADVANCED FINGERPRINT BIOMETRICS AND MEDICAL IMAGING

CROSS-REFERENCE TO RELATED APPLICATIONS

This patent application is a 35 USC 371 National Phase filing of International Application No. PCT/IB2017/053548, filed Jun. 14, 2017, which claims priority to U.S. Provisional Application No. 62/349,893, filed Jun. 14, 2016, the entire contents of which are incorporated by reference in their entirety without disclaimer.

BACKGROUND

1. Field of the Invention

This disclosure relates generally to methods, apparatuses, and systems that can implement RF imaging sensors for advanced security fingerprint biometrics and medical imaging.

2. Description of Related Art

Portable and wearable electronic devices have taken center stage in our everyday life handling sensitive personal information and critical tasks. As such, mobile device information security has become extremely important and traditional password protection methods are deemed impractical and vulnerable to hacking. Fingerprints are one of the most popular biometric identification methods and have already been deployed in portable devices. Current capturing methods record the fingerprint pattern formed by the ridges and valleys on the outer finger skin surface. These patterns are unique to every person and provide means of identification at significant security level. However, current scanners can be spoofed by phantom fingerprints using latent marks imprinted on glossy surfaces due to moisture present on the finger tips. To address this problem, sub-surface traits and sweat duct patterns can be exploited along with skin surface fingerprints. Toward this goal, millimeter and submillimeter waves, which can penetrate the outer skin layers as well as several packaging materials used in mobile electronics, can provide a promising scanning technology for advanced fingerprint biometrics. Millimeter and submillimeter waves (30 GHz-10 THz), (henceforth named Radio Frequencies or RF) is a relatively unexploited portion of the electromagnetic spectrum that provides superior spatial resolution compared to lower frequency electromagnetic waves (e.g. microwaves). Additionally, the proposed RF imaging modules can enable fingerprint scanning without requiring direct contact of the skin with the sensor. This can enable fingerprint scanning for users with protective gloves (e.g. laboratories). Additionally, the RF scanners could be placed behind the protective structure of the mobile/wearable device (e.g. underneath the cover glass).

Active imaging systems are very attractive at RF where room temperature sensors may not be sensitive enough and thermal body radiation may produce very weak signals. Therefore, a source is needed to illuminate the object scene, while the imaging sensors receive the reflected signal. Nevertheless, this global illumination scheme results in images with reduced dynamic range and the requirement for external illumination increases the overall size of the system. As a result, such topologies are deemed impractical for multi-pixel imaging systems where the sensor array is either in contact or very close to the object scene.

SUMMARY

This disclosure include embodiments of a radio-frequency (RF) imaging apparatus that may include a substrate, at least one RF source, at least one RF detector; and at least one linear imaging array. In some embodiments, the at least one linear imaging array may include at least one transmission line and one or more antennas. In some embodiments, the at least one RF source, the at least one RF detector, and the at least one linear imaging array may be monolithically integrated on the substrate. In some embodiments, the RF imaging apparatus may be configured to operate in a frequency range of 30 GHz-10 THz. In some embodiments, the at least one linear imaging array may include one or more RF switches, each of the one or more RF switches being coupled to at least one of the one or more antennas.

In some embodiments, the one or more RF switches may include one or more of microelectromechanical systems (MEMS) switches, photoconductive switches, or switches comprising electrically tunable materials (e.g., graphene, $MoS_2$, etc.). In some embodiments, the at least one RF source may be configured to propagate RF signals into skin tissue, the at least one linear imaging array may be configured to receive RF signals reflected from the skin tissue, and the at least one RF detector may be configured to record the detected RF signals. In some embodiments, a distance between the one or more antennas may have a width of less than 300 μm. In some embodiments, the one or more antennas may be connected in parallel via the at least one transmission line. In some embodiments, the one or more antennas may be one or more of slot dipole antennas and bowtie antennas. In some embodiments, the one or more antennas may be each have a separate RF source and a separate RF detector. In some embodiments, the one or more RF switches may each comprise a plurality of electrically tunable impedance sheets; a metal layer; and at least one insulating layer. In some embodiments, the at least one insulating layer may be disposed between the plurality of electrically tunable impedance sheets.

In some embodiments, an RF imaging apparatus may include a substrate; at least one RF source; a plurality of RF detectors; and a single traveling wave antenna. In some embodiments, the at least one RF source, the at least one RF detector, and the at least one linear imaging array are monolithically integrated on the substrate, and the RF imaging apparatus is configured to operate in a frequency range of 30 GHz-10 THz. In some embodiments, the RF imaging apparatus may further include a polarization selective surface. In some embodiments, the plurality of RF detectors may each comprise at least one detector antenna configured to support a same polarization as the travelling wave antenna. In some embodiments, the plurality of detector antennas may be orthogonally oriented to the travelling wave antenna. In some embodiments, the plurality of RF detectors may include one or more of direct detectors and coherent detectors.

In some embodiments, a computing system may be configured to perform RF imaging of skin tissue. The computing system may include at least one memory device, at least one processor, and at least one physical computer readable medium coupled to the at least one memory device. The at least one physical computer readable medium may comprise computer executable instructions that when executed by the at least one processor may be configured to propagate one or more RF signals into the skin tissue, receive one or more reflected RF signals from the skin tissue, record a digital state of each of the one or more reflected RF signals via one or more RF switches, construct a digital image of the skin tissue based on the recorded digital states of the one or more reflected RF signals, and determine an authentication state based on a comparison of the digital image and a prerecorded digital image of the skin tissue. In some embodiments, the RF signals are configured to penetrate multiple layers of skin tissue and are in a frequency range of 30 GHz-10 THz.

The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system, or a component of a system, that "comprises," "has," "includes" or "contains" one or more elements or features possesses those one or more elements or features, but is not limited to possessing only those elements or features. Likewise, a method that "comprises," "has," "includes" or "contains" one or more steps possesses those one or more steps, but is not limited to possessing only those one or more steps. Additionally, terms such as "first" and "second" are used only to differentiate structures or features, and not to limit the different structures or features to a particular order.

Any embodiment of any of the disclosed methods, systems, system components, or method steps can consist of or consist essentially of—rather than comprise/include/contain/have—any of the described elements, steps, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

The foregoing has outlined rather broadly certain features and technical advantages of embodiments of the present invention in order that the detailed description that follows may be better understood. Additional features and advantages will be described below. It should be appreciated by those having ordinary skill in the art that the conception and specific embodiment disclosed may be readily utilized as a basis for modifying or designing other structures for carrying out the same or similar purposes. It should also be realized by those having ordinary skill in the art that such equivalent constructions do not depart from the spirit and scope of the invention as set forth in the appended claims. Additional features will be better understood from the following description when considered in connection with the accompanying figures. It is to be expressly understood, however, that each of the figures is provided for the purpose of illustration and description only and is not intended to limit the present invention.

BRIEF DESCRIPTION OF THE DRAWINGS

The following drawings illustrate by way of example and not limitation. For the sake of brevity and clarity, every feature of a given method or system is not always labeled in every figure related to that method or system. Identical reference numbers do not necessarily indicate an identical feature. Rather, the same reference number may be used to indicate a similar feature or a feature with similar functionality, as may non-identical reference numbers.

FIGS. 1A-C show an exemplary RF imaging sensor and imaging capabilities according to an embodiment of the disclosure.

FIGS. 3A-F show exemplary main switching mechanisms according to an embodiment of the disclosure.

FIGS. 6A-D show an exemplary artificial skin structure and various subsurface images illustrating exemplary mapping of skin at certain imaging frequencies and a comparison of a measured image to an experimental simulated image according to an embodiment of the disclosure.

DETAILED DESCRIPTION OF ILLUSTRATIVE EMBODIMENTS

Figure 2A:
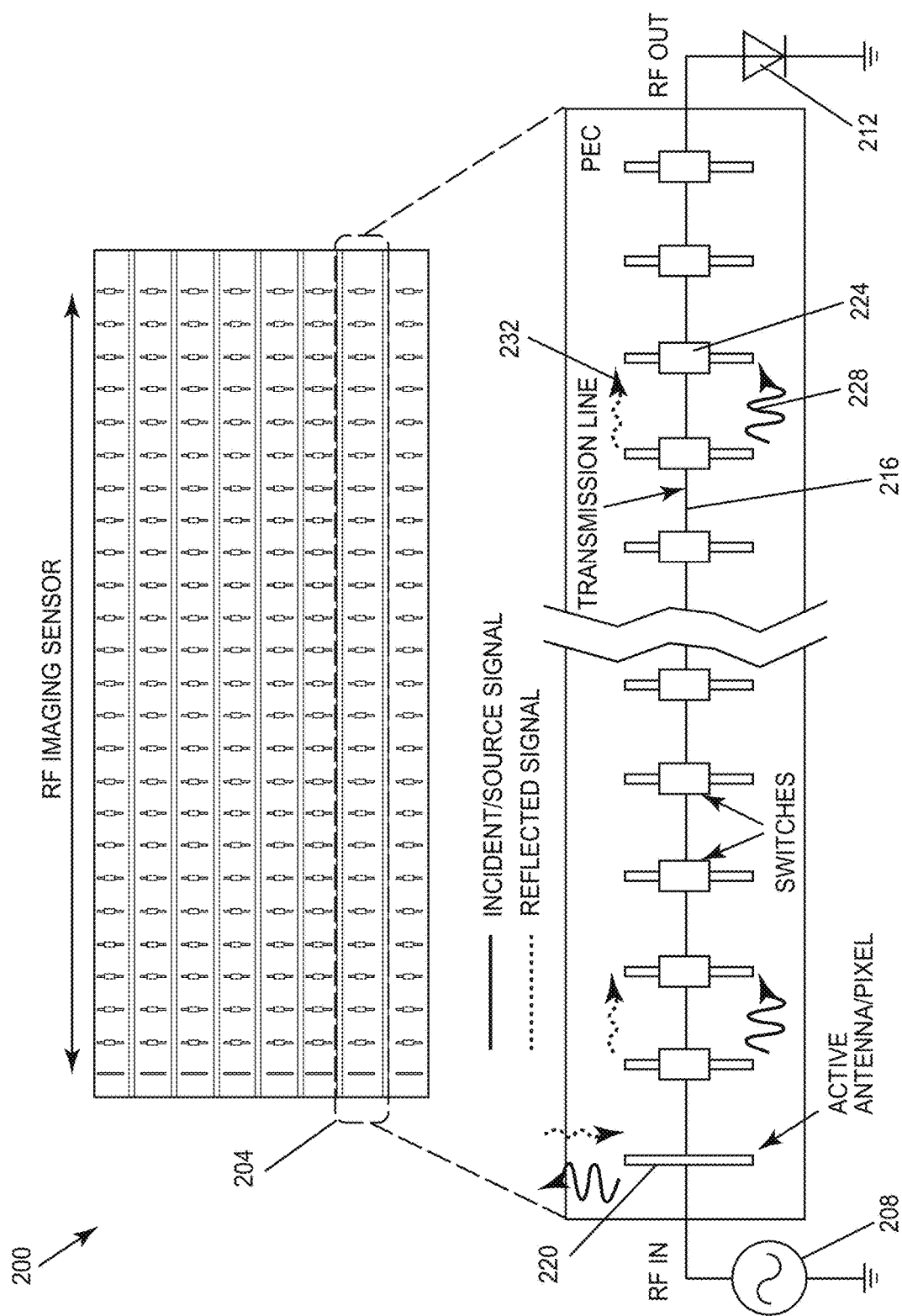
FIG. 2A shows an exemplary RF imaging sensor according to an embodiment of the disclosure.

In some embodiments, RF imaging sensors can have various active imaging topologies, including a Radio Frequency/RF (30 GHz-10 THz) imaging sensor. In some embodiments, the RF imaging sensor can have an array of antennas each connected to both their own separate source and detector. This topology may rectify some of the drawbacks of prior systems and can enable unique active imaging applications. In this type of RF imaging sensor, the object may be illuminated and imaged by the same device in real-time. The topology described herein may package sources, antenna-pixels, and ultrafast detectors on a planar structure forming a low profile sensor suitable for modern ultra-compact portable electronic devices. In the embodiments disclosed, a computing system having at least one processor may control the imaging modules to perform the functions described herein.

The imaging module described herein uses principles of antenna engineering, RF circuits, and imaging to create a novel topology for near-field imaging with RF waves. In some embodiments, on-chip antennas may be used for these types of sensors and may help minimize signal coupling losses while maintaining a simple fabrication process. Additionally, recent advances in semiconductor technology (using materials such as quartz, GaAs, GaN, InP, etc.) and nanofabrication techniques have resulted in extremely fast devices and circuits. For example, the cutoff frequency of BiCMOS oscillator/amplifiers may exceed 350 GHz and more sophisticated materials, such as InP technologies, have exhibited devices that have broken the 1 THz frequency barrier. Similarly, sensors are becoming increasingly faster and more sensitive allowing imaging systems to operate in millimeter and submillimeter waves. One embodiment of the disclosure may manipulate these short wavelengths efficiently and integrate the available ultra-fast semiconductor devices into a single substrate to enable, for the first time, high resolution and real-time skin tissue imaging with an extremely thin device (e.g., <300 μm).

In one disclosed embodiment, the imaging module may be a planar device that requires no focusing elements (e.g., mirrors, lenses) and may feature an ultra-thin profile (e.g., <0.3 mm) to enable integration in portable and wearable devices. In some embodiments, the module may be comprised of an RF source module, RF sensors, and an antenna array topology that may operate in the 30 GHz-10 THz range. The array topology may be monolithically integrated with the RF source and detectors, and fabricated on a low loss quartz substrate, although other suitable substrate materials can be used. In some embodiments, several linear antenna arrays may be placed side by side to form a 2D array sensor. The linear arrays may be comprised of planar waveguides that may connect several antennas in parallel. On the waveguides' input, an RF source may transmit the RF signal that may be split between the antennas and the RF detector, located at the output of each individual waveguide. As such, when the sensor array is placed on the skin, the RF source may illuminate the tissue and concurrently the RF sensors may detect the reflected signals. These RF signals may propagate through the skin layers and provide anatomical information about the tissue morphology in the form of a digital image. The image acquisition may be achieved by serially recording the detected RF signal from each antenna column with the use of RF switches. In some embodiments, when the switch is in an ON state, the antenna may be electrically connected to the waveguide and may transmit/receive RF signals. Concurrently, the remaining switches on the linear antenna array may be in an OFF state, deactivating the rest of the antennas. Thus, the switches may be serially scanned and all corresponding DC signals may be recorded on the RF detectors at the end of the waveguides. The resulting 2D distribution of DC signals may correspond to the skin subsurface anatomy. In some embodiments, the antenna switching mechanism can be implemented using MEMS technology or electrically tunable impedance sheets (e.g., graphene, $MoS_2$, etc.). MEMS switches are commonly used in RF devices and may offer superior switching performance. Alternatively, electrically tunable impedance sheets can be placed at the interconnection of the antenna and the waveguide. Under certain DC biasing, these electrically tunable impedance sheets may become conductive, providing an electrical connection between the antenna and the waveguide.

Herein, an RF imaging module for active mm wave and sub-mm wave imaging is presented. The new layout may enable monolithic integration of a source-antenna-detector on a single substrate and may allow the implementation of large-format imaging sensors. Additionally, such a topology may be extremely low profile (e.g., <300 μm) and may be suitable for integration in portable electronic devices. FIGS. 1A-C show an exemplary RF imaging chip 100 and corresponding imaging capabilities according to an embodiment of the disclosure. FIG. 1A illustrates an exemplary RF sensor 100 that can be used for mobile biometrics and/or medical imaging. In the embodiment shown, the sensor can comprise on-chip antennas integrated on a low profile, planar device. FIG. 1B shows a side view of the sensor 100 shown in FIG. 1A when placed on an area or portion of skin 104. In the embodiment shown, one or more RF waves 108 can penetrate through the skin layers to reveal the inner skin morphology. FIG. 1C shows an exemplary multilayer skin morphology corresponding to the skin portion shown in FIG. 1B. In the embodiment shown, imaging sensors can provide three "layer" information from the top and inner skin tissue structure. Human finger skin is comprised of several tissue layers, each one with a unique morphology, as shown in FIG. 1B. In the embodiment shown, sensor 100 can detect and provide images of skin surface undulations 112, a sweat duct pattern 116, and epidermis undulations 120. Current fingerprint biometric sensors image ridges and valleys of skin surfaces and use their pattern to uniquely identify the users. RF waves (30 GHz-10 THz) offer the opportunity to retrieve the morphology of subsurface skin tissue and drastically limit imposters from gaining unauthorized access. In some embodiments, the images shown in FIGS. 1B-C can be digital images constructed based on recorded digital states of reflected RF signals. In the embodiments shown, the digital states may correspond to ON/OFF states of switches. In some embodiments, a computer system having at least one processor may have a database containing various prerecorded or pre-stored digital images of skin tissue corresponding to different users. In some embodiments, the computer system may record the digital states of reflected RF signals, construct images based on the recorded digital state, and compare the constructed digital images with one or more of the prerecorded digital images stored in the database. If the computer system determines that the constructed digital images match one or more of the prerecorded digital images, the computer system authenticates the user. If the computer system determines that the constructed digital images do not match one or more of the prerecorded digital images, the computer system may deny authentication to the user.

FIG. 2A illustrates an exemplary large-format RF imaging sensor 200 according to an embodiment of the disclosure. In the embodiment shown, the RF sensor 200 has a sensor that is comprised of parallel cascaded linear arrays 204. Each linear array segment may be fed by a source 208 (i.e., RF IN) and terminated to an ultra-fast detector 212 (i.e., RF OUT). RF imaging sensors may consist of several independent linear imaging arrays that can be monolithically cascaded in parallel and form large-format active sensors (e.g., >1,000 pixels). Each linear segment may be comprised of an RF source 208, a transmission line (TL) 216, one or more antennas 220, and an ultra-fast detector 212. In the embodiment shown, one or more of the antennas 220 are coupled to switches 224. In some embodiments, the antennas 220 used may be slot dipole antennas that couple radiation efficiently into materials with a high index of refraction (e.g., >1). However, alternative electromagnetic radiators/antennas can also be employed (i.e. bowtie antennas, strip antennas, etc.).

Moreover, the design presented in FIG. 2A can be miniaturized to increase the pixel density.

Figure 2B:
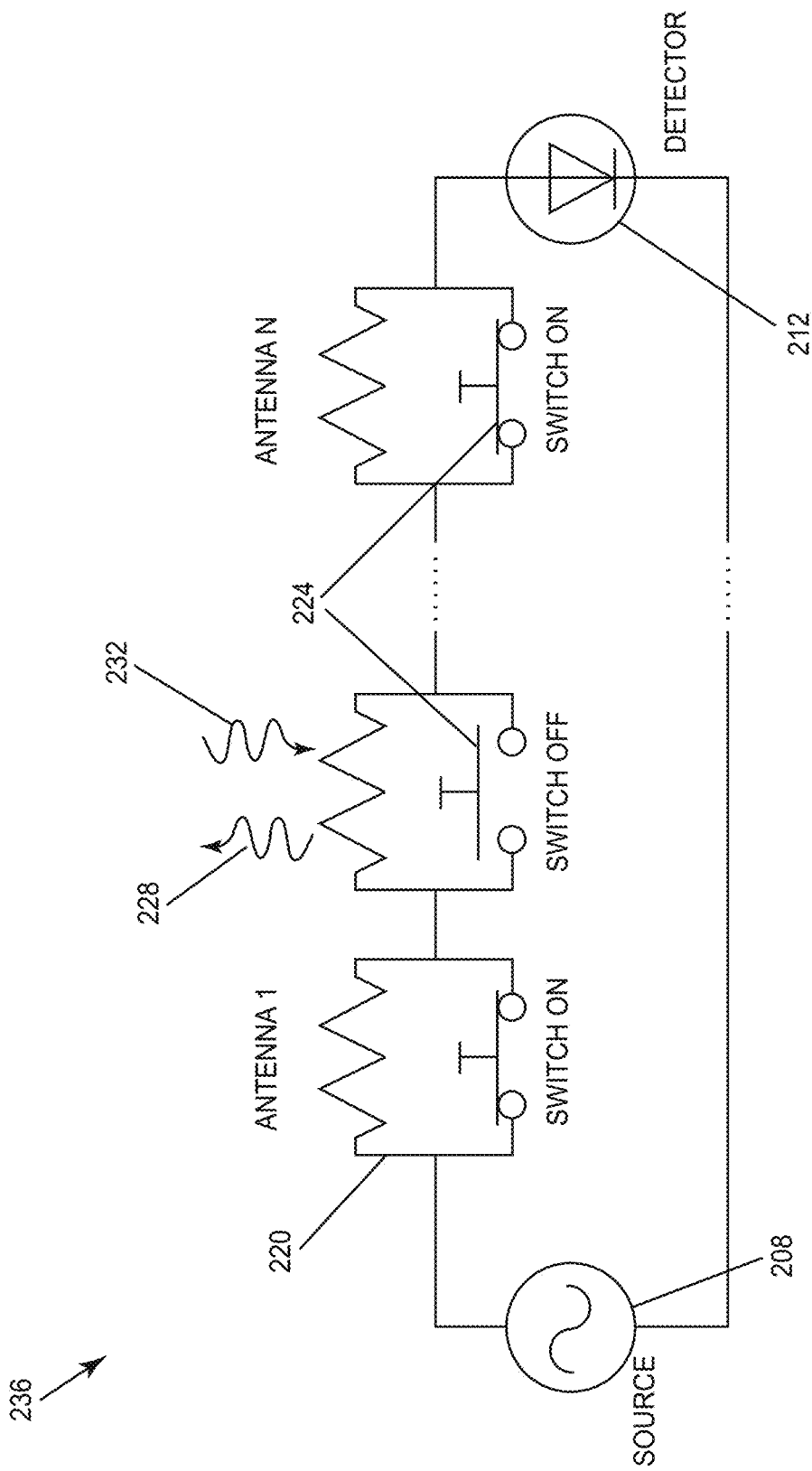
FIG. 2B shows a linear segment equivalent circuit contained in the RF imaging sensor shown in FIG. 2A.
Figure 2C:
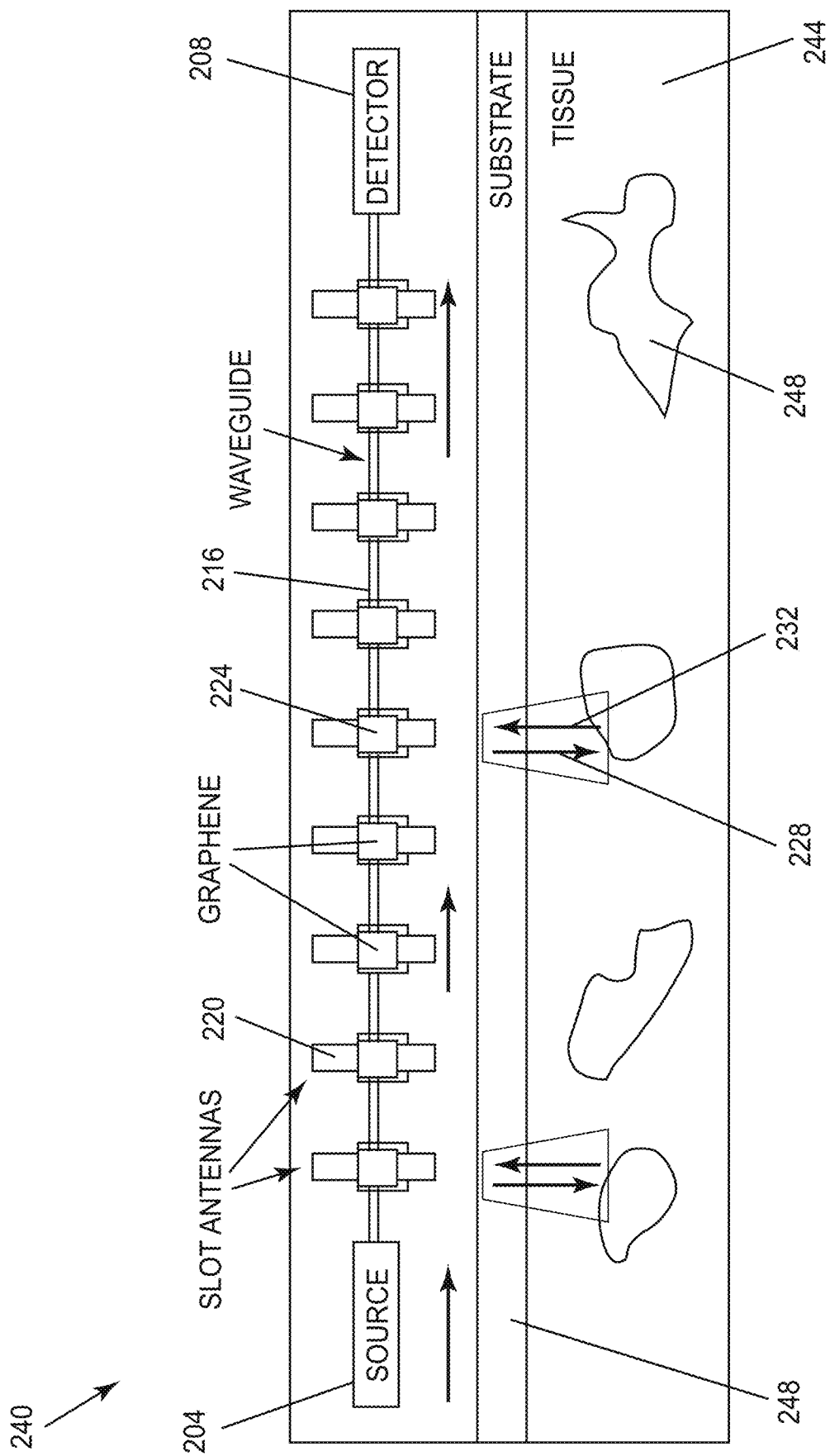
FIG. 2C shows a view of a linear segment of the exemplary RF imaging sensor of FIG. 2A disposed against skin tissue according to an embodiment of the disclosure.

Each linear array segment 204 may be fed by an RF source and may be terminated to an ultrafast detector, as depicted in FIG. 2A. Before the signal reaches the detector 212, a properly switched antenna (e.g., active) may radiate a portion of the propagating signal. In the embodiment shown, incident or source signals 228 are shown with a higher amplitude and reflected signals 232 are shown with a lower amplitude. The antenna input impedance may allow approximately half of the power to couple into the active antenna and the remaining signal may propagate along the TL 216 to reach the detector 212. Meanwhile, the backscattered signal may be received by the same antenna and may be fed back into the TL 216. Similarly, half of the backscattered signal may reach the detector 212 and the rest of the backscattered signal may be dissipated on the source resistor. FIG. 2B illustrates an equivalent circuit 236 of a linear array segment 204. In the embodiment shown, when the switches 224 are ON, the slot antennas 220 are short-circuited and the only antenna that transmits incident or source signals 228 and receives reflected signals 232 is the one with the switch in OFF state (i.e., open circuit). As such, a proper switching scheme, repeated in every linear segment 204, may allow sequential signal sampling from every antenna on the 2D array. The magnitude of the recorded signals may depend on the material properties of the object located beneath the corresponding antennas. FIG. 2C illustrates a view 240 of a linear segment 204 of the exemplary RF imaging sensor 200 of FIG. 2A disposed against skin tissue 244 according to an embodiment of the disclosure. In the embodiment shown, a substrate 248 of a linear array segment 204 may be placed directly on an area of skin tissue 244 that is desired to be imaged. In the embodiment shown, incident or source signals 228 are transmitted from antennas 220 and reflected signals 232 are received by antennas 220 to detect and image skin undulations and/or sweat glands 248. Although FIG. 2C illustrates an embodiment that uses graphene for switches 224, other types of switches and/or electrically tunable impedance materials can be used, as discussed below.

As previously mentioned, a switching mechanism 224 may be integrated in the array 204 to enable rapid electronic scanning of the object scene. For this purpose, electrically tunable impedance sheets (e.g., graphene), photoconductive switches, or MEMS switches can be used to achieve efficient and fast signal switching among the antenna elements 220. For example, switching can be achieved by electrically tuning the conductivity of a strategically positioned electrically tunable impedance sheet, thus approximating an open or short circuit, which would constitute ideal switching. FIGS. 3A-F show exemplary main switching mechanisms 300 having one or more electrically tunable impedance sheets 304 according to an embodiment of the disclosure. As depicted in FIG. 3A, when electrically tunable impedance sheet 304 is biased by an external electric field, the sheet conductivity may increase dramatically (e.g., ~10 fold). As a result, the electric current 308 may bypass the slot dipole antenna 312 and inhibit pixel illumination (e.g., OFF state). The OFF state occurs when the electrically tunable impedance sheet 304 is electrically biased. On the contrary, an unbiased electrically tunable impedance sheet 304 may exhibit a large resistance (e.g., 5,000Ω/☐—Ohms-per-square) as shown in FIG. 3B. This may route the electric current 308 around the slot antenna 312 and may allow the antenna to radiate (e.g., ON state). In the embodiments shown, the ON state occurs when the electrically tunable impedance sheet 304 is unbiased and exhibits low electrical conductivity. Similarly, a network of MEMS or photoconductive switches 316 can be employed to enable rapid image acquisition. FIGS. 3C and 3D depict a photoconductive switching approach. This mechanism is based on the premise that a dielectric's conductivity can be controlled by illuminating it with an external optical source 320. Illumination from the external optical source 320 may create additional carriers in the substrate 324, thus increasing material conductivity in the vicinity of the illuminated area. The substrate 324, which may comprise Si, GaAs, or the like, can also be doped in order to achieve higher conductivity during the illumination. In photoconductive switching, the slot antenna 312 may be illuminated and may deactivate the antenna. When the dielectric substrate 324 is illuminated, a high conductivity area may be formed that allows the current to short-circuit the antenna 312. In the case of no illumination, the antenna 312 may be active.

Additionally, electrically tunable impedance based MEMS 328 may be activated by applying an electric field bias between two conductive layers (e.g., graphene) as shown in FIG. 3E. FIG. 3E shows an example of a MEMS-based switch 328 having two conductive sheets 332, 336 (e.g., graphene) located on the feed of a slot dipole antenna 312. When electric bias is applied between the two conductive layers, the upper sheet 332 may make contact with the lower sheet 336 and form a high conductivity path for the current that may bypass the slot antenna 312 (e.g., OFF state). On the other hand, in the absence of external bias, the upper sheet 332 may retract and behave as an open circuit for the current (e.g., ON state). These states of a conductive sheet-based MEMS 328 are illustrated in FIG. 3F.

Figures 4A, 4B, 4C:
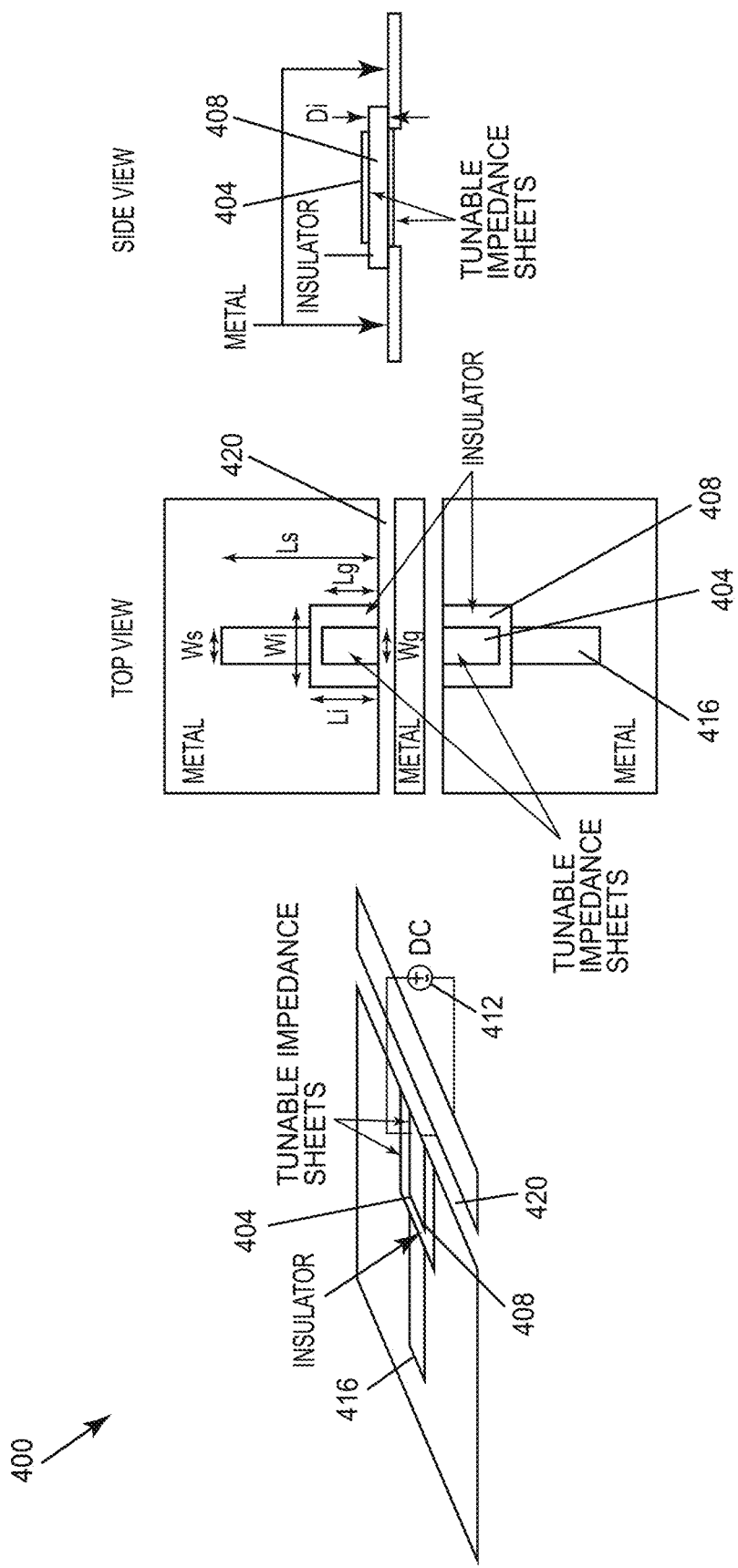
FIGS. 4A-C show an exemplary biased electrically tunable impedance sheet switch according to an embodiment of the disclosure.

From the aforementioned switching mechanisms, electrically tunable materials (e.g., graphene, $MoS_2$, etc.) stand out mainly due to the low manufacturing cost, electronics compatibility, and reliability compared to standard MEMS. As mentioned above, the resistance of these electrically tunable materials can be tuned by applying an external electric field. FIGS. 4A-C illustrate a principle of operation of a biased electrically tunable impedance sheet switch 400. In some embodiments, the electrically tunable impedance sheet switch can be implemented using graphene or other electrically tunable materials and may be embedded in RF imaging sensors operating in the 30 GHz-10 THz band. For different operating spectrums, the dimensions can be scaled respectively. To achieve this external field biasing, it may be preferred to use two conductive sheets 404 as shown in FIG. 4A. In the depicted example, the switch 400 may consist of two electrically tunable layers/sheets 404, a separating insulator 408, and an external voltage source 412 to achieve the tunable biasing. This topology may minimize the parasitic effects of having a metallic biasing pad in the vicinity of the antenna 416. A top view of an element of the array integrated with the electrically tunable impedance switch 400 is shown in FIG. 4B. In the embodiment shown, the dimensions are Ws=Wg=10 μm, Ls=200 μm, Lg=2·Wg, Li=1.1·Lg and Wi=1.1·Wg. In some embodiments, both electrically tunable impedance sheets 404 may have the same dimensions, but the insulator 408 that separates them may be slightly wider to avoid the distortion of the biasing field. A commonly used insulator is $SiO_2$ but other suitable insulators such as a layer of polymethylmethacrylate (PMMA) can be also be used for isolation. Alternatively, other higher $\varepsilon_r$ materials such as $HfO_2$ can be used as the insulating material to minimize the dimensions of the switch 400 even further. In some embodiments, the insulator 408 can be replaced by other materials like ionic liquid in order to enhance the switching ratio of the switch 400. The ratio between the width and length of the electrically tunable materials (n=Lg/Wg) can vary in order to achieve optimum impedance matching between the antennas 416 and the transmission line 420. As such, alternative antenna topologies might require a different ratio n for maximum image contrast. In FIG. 4C, a side view of the switch 400 shows the layered structure of the switch. In some embodiments, the thickness Di of the insulator 404 can be approximately 80-100 nm.

RF imaging sensors can be implemented in various imaging scenarios depending on the application requirements. For example, RF imaging sensors can be used for near field imaging by placing the sensor array either very close or in contact with the object such as in non-destructive sublayer sensing (paint coatings) or medical imaging (skin tissue). Alternatively, the sensor array can be placed behind a hyper-hemispherical lens and enable longer distance imaging. In both scenarios, the sensor may operate as a continuous wave (CW) monostatic radar, transmitting and receiving the RF signals from the same pixel location.

Figure 5A:
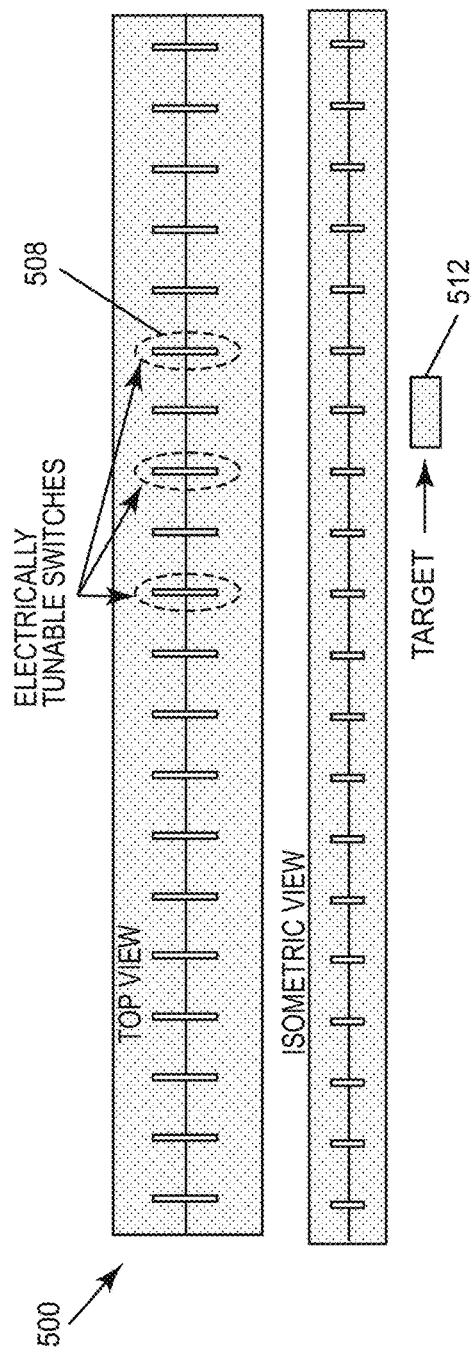
FIGS. 5A-D show exemplary RF imaging sensor structures for illustrating a full-wave model analysis of image performance and corresponding graphs illustrating one or more extracted images using electrically tunable impedance sheet switches according to an embodiment of the disclosure.
Figure 5B:
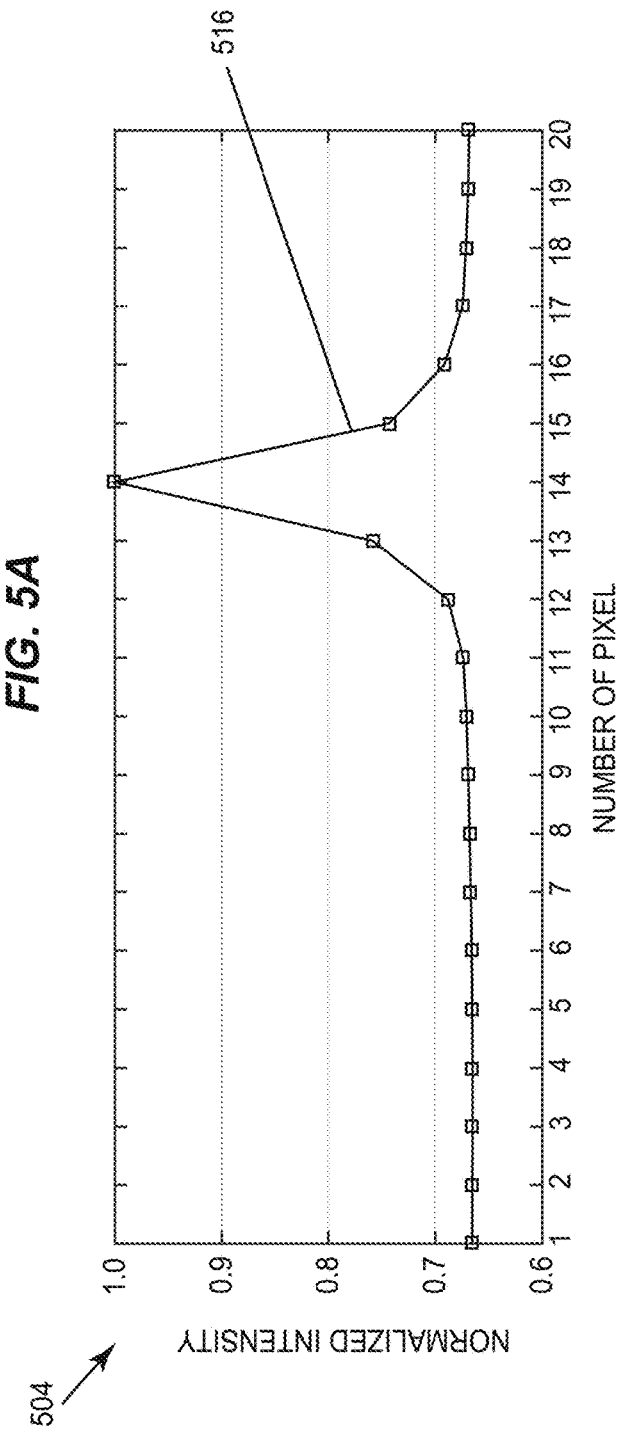
Figure 5C:
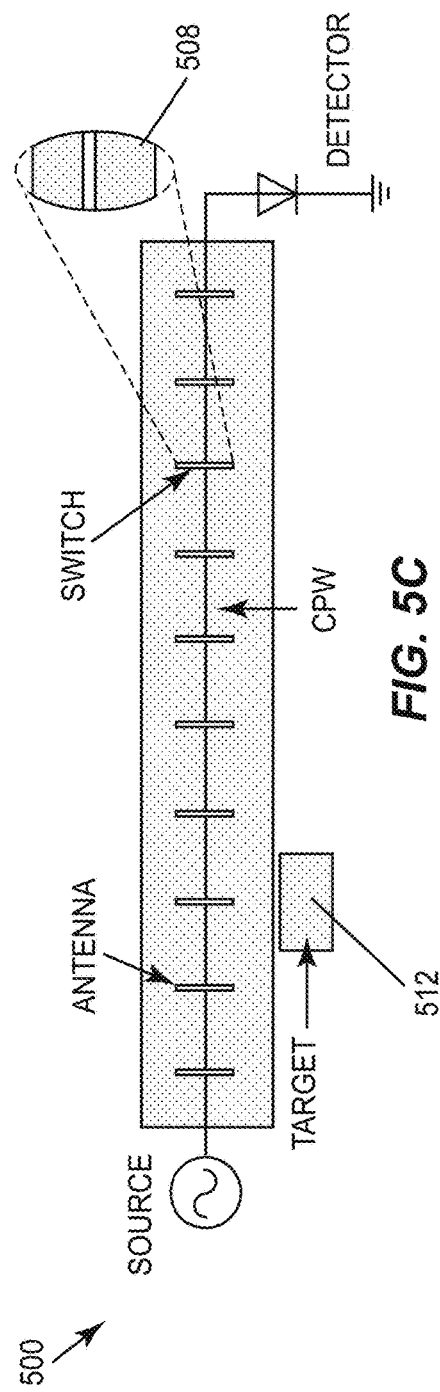
Figure 5D:
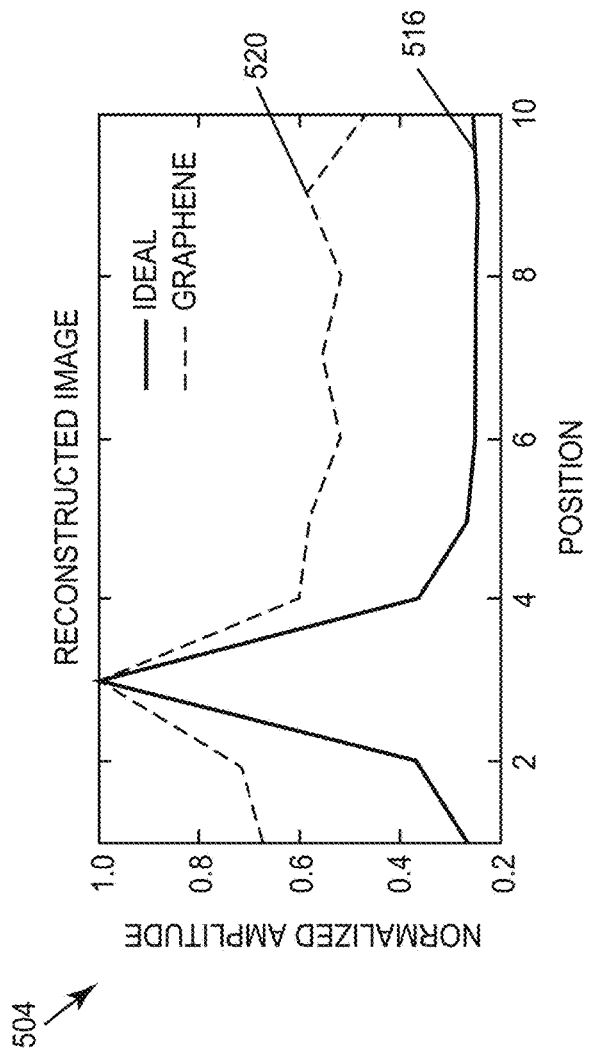

FIGS. 5A-D show exemplary RF imaging sensor structures 500 for illustrating a full-wave model analysis of image performance and corresponding graphs 504 illustrating one or more extracted images using electrically tunable impedance sheet switches 508 according to an embodiment of the disclosure. In these figures, an example of near field imaging through a commercial full wave electromagnetic sensor is illustrated. In this embodiment, a RF imaging sensor may be placed in direct contact with the outer skin surface and each antenna may illuminate and receive the backscattered signal from a small area underneath the skin surface (e.g., individual pixel area). For example, FIGS. 5A and 5C illustrate a full-wave model analysis of a linear twenty element RF sensor imaging performance by placing one metallic object (i.e., target 512) 500 µm below the array level. In some embodiments, the substrate may be quartz having a relative dielectric permittivity of εr=3.78. The recorded signal on the simulated detector may be used to form the images presented in FIGS. 5B and 5D for the case of electrically tunable impedance sheet switches 708 having a 1:10 switching ratio for the ON/OFF case. The element pitch in the embodiment shown is 350 µm and the unbiased and biased electrically tunable impedances are Zu=500Ω/□ and Zb=5,000Ω/□, respectively. In the embodiment shown, the performance of an ideal switch 716 that can open the circuit to an infinite resistance or act as a perfect conductor without any losses is compared to the performance of an electrically tunable impedance sheet switch (e.g., graphene) 520. Advanced electrically tunable impedance compounds can be used to further increase the switching performance and improve image contrast.

FIGS. 6A-D show an exemplary artificial skin structure 600 and various subsurface images illustrating exemplary mapping of skin at certain imaging frequencies and a comparison of a measured image to an experimental simulated image according to an embodiment of the disclosure. In the embodiments shown, RF imaging tests were conducted on an artificial finger skin model (an exemplary portion of which is shown in FIG. 6A) to mimic the morphology and electrical properties of actual human tissue. The model was 3D printed using photopolymer resin with relative permittivity εr ~3, closely matching the expected permittivity of the epidermis. In the embodiment shown, helical hollow structures connect the top surface of the model to a water tank underneath the epidermis, forming an artificial sweat duct structure. The tank and sweat ducts are filled up with water to emulate the highly absorptive dermis tissue as well as the presence of sweat in the ducts.

An exemplary RF imaging sensor structure was placed on the top surface of the model. The model was fixed on a 2D raster scanner and a monopole probe antenna was placed close to the skin surface. As such, 2D images of the tissue were recorded in the 10-20 GHz band to account for the model scale (1:20). FIGS. 6B and 6C show images at different frequencies. In some embodiments, air gaps may be present in valleys of the skin surface underneath the RF imaging sensor structure that can create large reflections that don't image well. As such, imaging of the valleys may be more effective at lower frequencies. This effect is shown in FIGS. 6B and 6C. In the embodiments shown, the exemplary model shown in FIG. 6A was imaged at two different frequencies—14 and 16 GHz that correspond to 280 and 320 GHz for the actual skin dimensions. As shown, the patterns for ridges 604 and valleys 608 are present throughout the entire measured spectrum. The ridges 604 are more prominently shown in FIG. 6B, which corresponds to imaging at 320 GHz. In contrast, the valleys 608 are more prominently shown in FIG. 6C, which corresponds to imaging at a lower frequency of 280 GHz. However, the sweat ducts 612 are only detected at certain frequencies. This property can be used to differentiate between a spoof fingerprint that consists of only the surface undulations and the actual tissue consisting of subsurface traits.

In the embodiments shown, the imaging was able to reconstruct the ridges and valleys pattern of the model as well as locate the sweat ducts underneath. The acquired images were in close agreement with image results from a simulated numerical model. FIG. 6D depicts a comparison between the measured image of the skin model and a simulated image created from the simulated numerical model. The similarities between the two images confirm that the detected sweat ducts 612 correspond to actual sweat duct structures and are not merely attributable to standing wave resonances within ridge/valley confinements.

Figure 7:
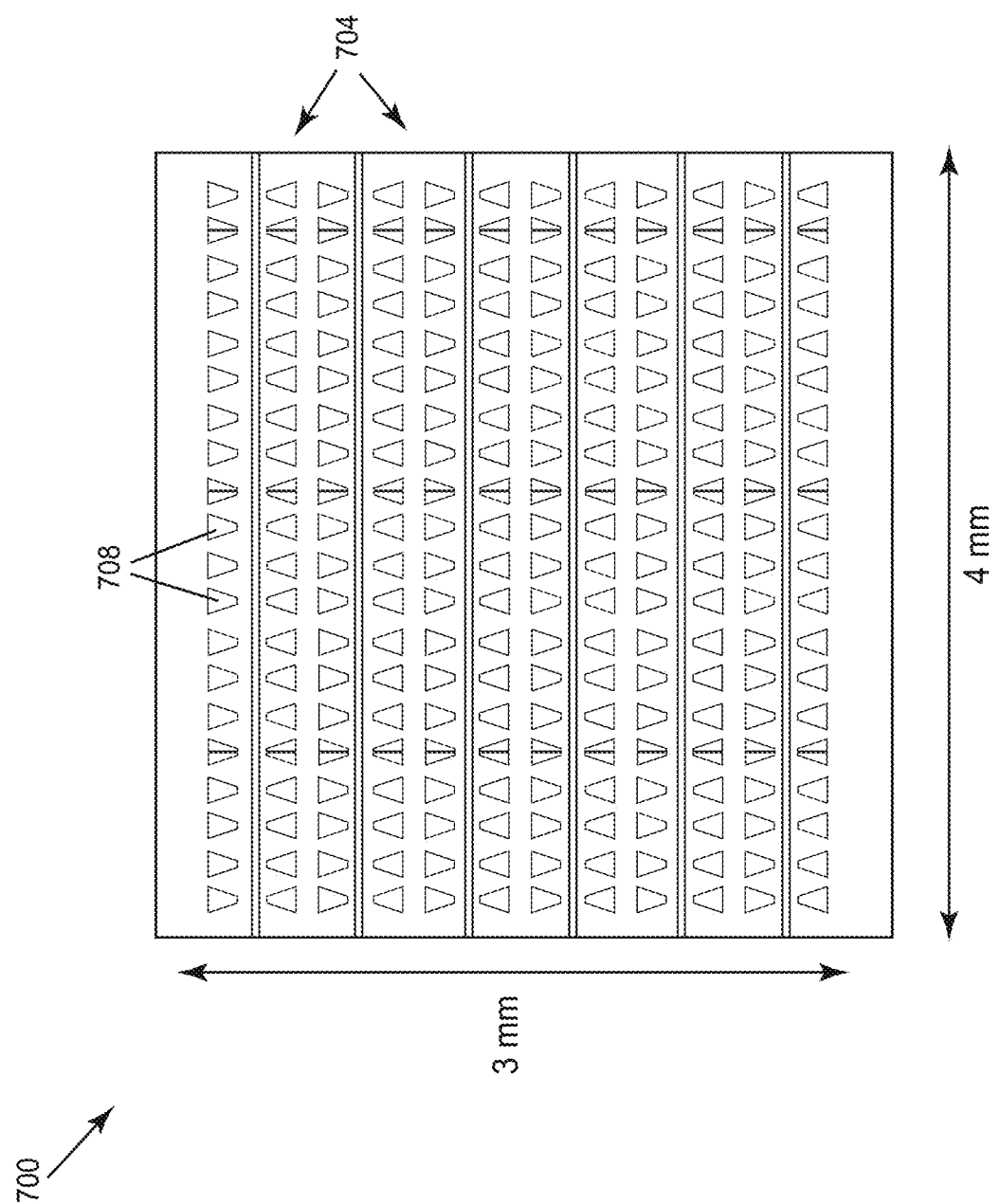
FIG. 7 shows an exemplary RF imaging sensor array according to another embodiment of the disclosure.

FIG. 7 shows an exemplary RF imaging sensor array 700 according to another embodiment of the disclosure. In the embodiment shown, RF imaging sensor array 700 has multiple parallel cascaded linear arrays 704, similar to those shown in FIG. 2A. However, RF imaging sensor array 700 uses bowtie antennas 708 instead of the slot antennas 220 shown in FIG. 2A. This structure works similarly to the embodiment shown in FIG. 2A but may have a different element pitch (i.e., distance between antennas), a different line pitch (i.e., distance between transmission lines), and may operate at different frequency ranges. In the embodiment shown, the RF imaging sensor array 700 is 4 mm long and 3 mm wide but other suitable dimensions may be used.

Figure 8B:
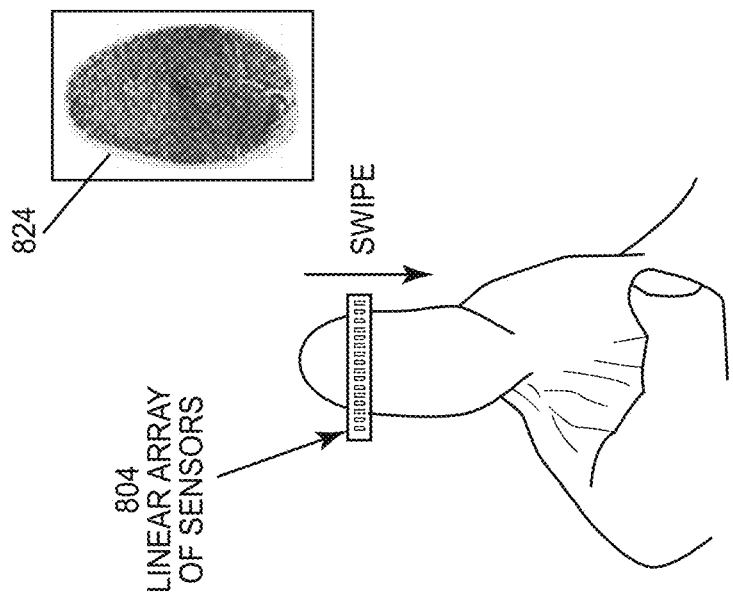
FIGS. 8A-B show an exemplary RF imaging sensor fingerprint scanner according to an embodiment of the disclosure.
Figure 8A:
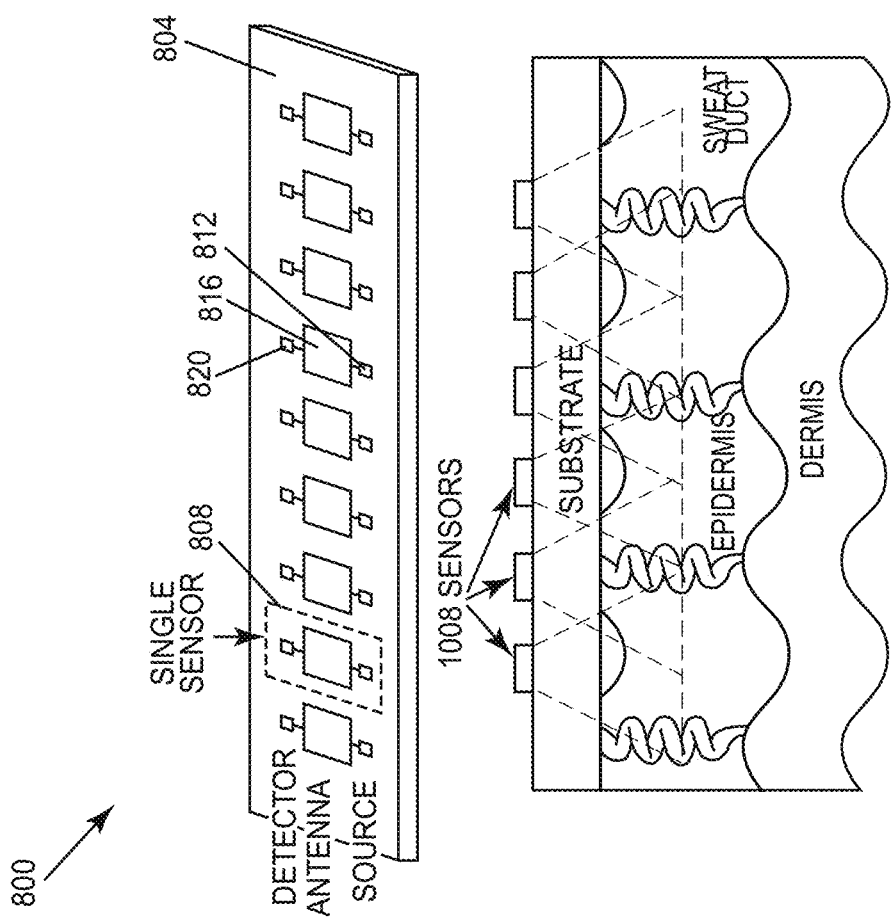

FIGS. 8A-B show an exemplary RF imaging sensor fingerprint scanner 800 according to an embodiment of the disclosure. In the embodiment shown, the fingerprint scanner 800 is comprised of a linear sensor array 804 having one or more sensors 808 each having a source 812, antenna 816, and a detector 820. In the embodiment shown, a fingerprint image 824 is synthesized using a finger linear motion (swiping) over the surface of the linear sensor array 804. When swiping, the finger skin is in touch with the sensor array substrate and moves normal to the longer direction of the linear sensor array 804 while the sensors captures one or more linear images. In some embodiments, the finger may be swiped normal to the shorter direction of the linear sensor array 804. In the embodiment shown, the sensors illuminate the underlying tissue region of the finger and record the reflected signals, which are then used for image reconstruction. In some embodiments, the 2D fingerprint image 824 can be synthesized by combining the various linear images together. The linear sensor array 804 can be comprised of the previously disclosed antenna topologies. However, in the embodiment shown, each antenna 816 is connected to its own individual source 812 and detector 820. This structure eliminates the need of using RF switches as shown in the previously discussed embodiments.

Figure 9:
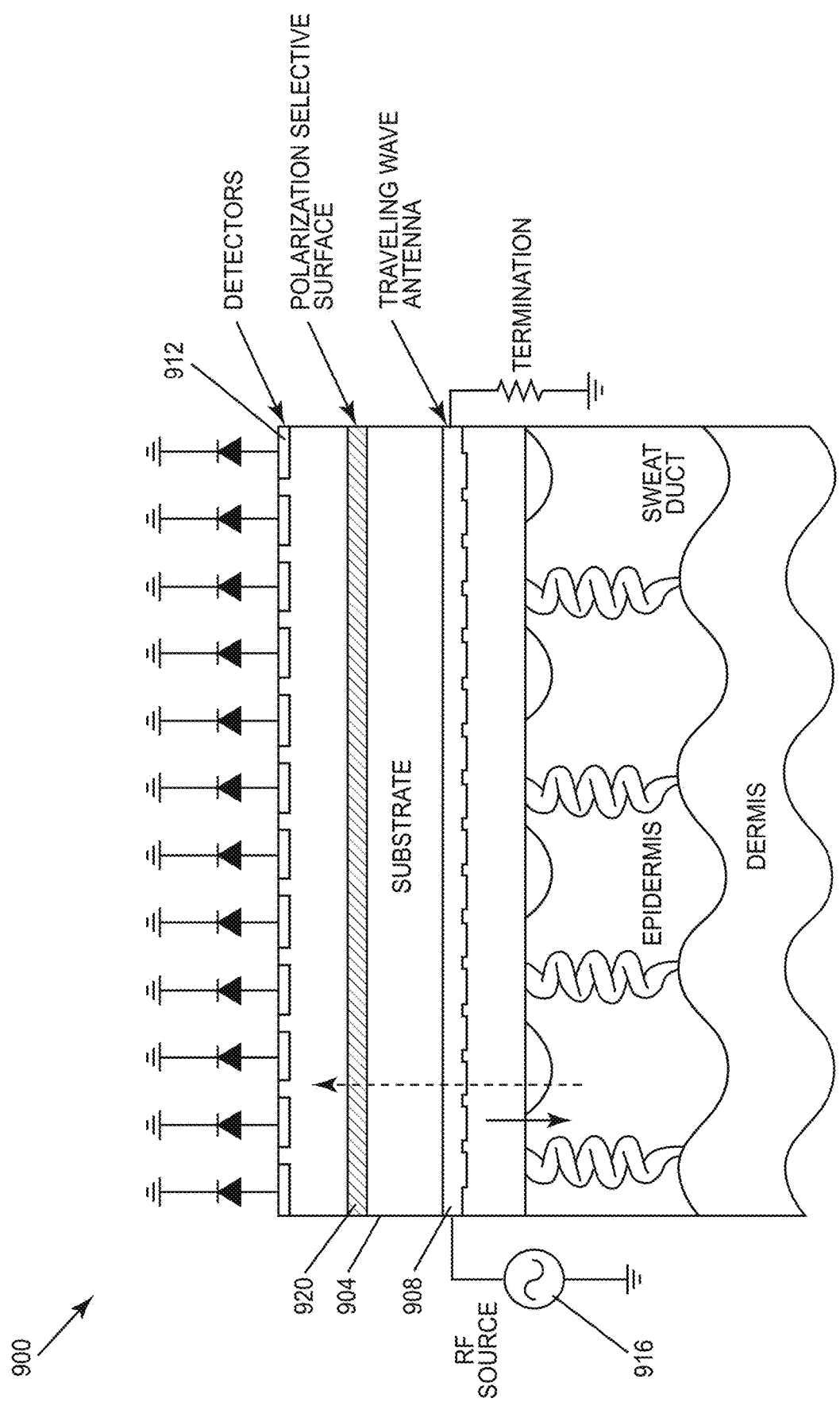
FIG. 9 shows an exemplary RF imaging sensor structure according to another embodiment of the disclosure.

FIG. 9 shows an exemplary RF imaging sensor structure 900 according to another embodiment of the disclosure. In the embodiment shown, the RF imaging sensor can be comprised of a substrate 904, a linearly polarized, 2D travelling wave antenna 908, and a linearly polarized, 2D array of mmW/THz detectors 912. In the embodiment shown, the travelling wave antenna 908 is fed by an RF source 916 and can serve as a tissue illuminator. As such, the RF waves can illuminate the skin and the reflected waves can be detected by the 2D detectors 912 located above the traveling wave antenna 908. In some embodiments, the detectors 912 are disposed on a surface of the substrate 904 and traveling wave antenna 908 is disposed within the substrate 904 in a configuration to be disposed between the skin tissue and the detectors 912. In some embodiments, the 2D detector array can be comprised of either direct or coherent detectors. In some embodiments, the detectors 912 may have antennas that can support the same polarization as the travelling wave antenna 908 in order to record co-polarization scattered fields. In other embodiments, detector antennas and the travelling wave antenna 908 can be orthogonally oriented in order to record the cross-polarization scattered fields. Alternatively, a polarization selective surface 920 can be introduced between the travelling wave antenna 908 and the detectors 912 to allow only the desired polarization to be detected by sensor antennas. In the embodiment shown, the polarization selective surface 920 is oriented parallel to the travelling wave antenna 908.

It may be appreciated that the functions described above may be performed by multiple types of software applications, such as web applications or mobile device applications. If implemented in firmware and/or software, the functions described above may be stored as one or more instructions or code on a non-transitory computer-readable medium. Examples include non-transitory computer-readable media encoded with a data structure and non-transitory computer-readable media encoded with a computer program. Non-transitory computer-readable media includes physical computer storage media. A physical storage medium may be any available medium that can be accessed by a computer. By way of example, and not limitation, such non-transitory computer-readable media can comprise RAM, ROM, EEPROM, CD-ROM or other optical disk storage, magnetic disk storage or other magnetic storage devices, or any other physical medium that can be used to store desired program code in the form of instructions or data structures and that can be accessed by a computer. Disk and disc includes compact discs (CD), laser discs, optical discs, digital versatile discs (DVD), floppy disks and Blu-ray discs. Generally, disks reproduce data magnetically, and discs reproduce data optically. Combinations of the above are also included within the scope of non-transitory computer-readable media. Moreover, the functions described above may be achieved through dedicated devices rather than software, such as a hardware circuit comprising custom VLSI circuits or gate arrays, off-the-shelf semiconductors such as logic chips, transistors, or other discrete components, all of which are non-transitory. Additional examples include programmable hardware devices such as field programmable gate arrays, programmable array logic, programmable logic devices or the like, all of which are non-transitory. Still further examples include application specific integrated circuits (ASIC) or very large scale integrated (VLSI) circuits. In fact, persons of ordinary skill in the art may utilize any number of suitable structures capable of executing logical operations according to the described embodiments.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the disclosed methods, devices, and systems are not intended to be limited to the particular forms disclosed. Rather, they include all modifications and alternatives falling within the scope of the claims, and embodiments other than those shown may include some or all of the features of the depicted embodiment. For example, components may be combined as a unitary structure and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A radio-frequency (RF) imaging apparatus comprising:
a substrate;
at least one RF source;
at least one RF detector;
at least one linear imaging array comprising:
at least one transmission line; and
one or more antennas; and
one or more RF switches, each of the one or more RF switches being coupled to at least one of the one or more antennas and comprising:
a plurality of electrically tunable impedance sheets;
a metal layer; and
at least one insulating layer disposed between the plurality of electrically tunable impedance sheets;
where the at least one RF source, the at least one RF detector, and the at least one linear imaging array are monolithically integrated on the substrate, and
where the RF imaging apparatus is configured to operate in a frequency range of 30 GHz-10 THz.

2. The apparatus of claim 1, where the one or more RF switches comprise one or more of microelectromechanical systems (MEMS) switches, photoconductive switches, or switches comprising one or more electrically tunable materials.

3. The apparatus of claim 2, where the electrically tunable material is graphene.

4. The apparatus of claim 1, where the at least one RF source is configured to propagate RF signals into skin tissue, the at least one linear imaging array is configured to receive RF signals reflected from the skin tissue, and the at least one RF detector is configured to record detected RF signals.

5. The apparatus of claim 1, where a distance between the one or more antennas comprises a width of less than 300 μm.

6. The apparatus of claim 1, where the one or more antennas are connected in parallel via the at least one transmission line.

7. The apparatus of claim 1, where the one or more antennas are one or more of slot dipole antennas and bowtie antennas.

8. The apparatus of claim 1, where the one or more antennas each have a separate RF source and a separate RF detector.

9. The apparatus of claim 1, further comprising a polarization selective surface.

10. The apparatus of claim 1, wherein the one or more antennas comprise a traveling wave antenna.

11. The apparatus of claim 10, where the at least one RF detector comprises at least one detector antenna configured to support a same polarization as the travelling wave antenna.

12. A radio-frequency (RF) imaging apparatus comprising:
   a substrate;
   at least one RF source;
   a plurality of RF detectors;
   a single traveling wave antenna; and
   a polarization selective surface,
   where the at least one RF source, the at least one RF detector, and the single traveling wave antenna are monolithically integrated on the substrate, and
   where the RF imaging apparatus is configured to operate in a frequency range of 30 GHz -10 THz.

13. The apparatus of claim 12, where the plurality of RF detectors each comprise at least one detector antenna configured to support a same polarization as the travelling wave antenna.

14. The apparatus of claim 13, where the at least one detector antenna is orthogonally oriented to the travelling wave antenna.

15. The apparatus of claim 12, further comprising one or more RF switches, each of the one or more RF switches being coupled to at least one of the single traveling wave antenna or one or more detector antennas.

16. The apparatus of claim 15, where the one or more RF switches each comprise:
   a plurality of electrically tunable impedance sheets;
   a metal layer; and
   at least one insulating layer disposed between the plurality of electrically tunable impedance sheets.

17. A computing system configured to perform radio-frequency (RF) imaging of skin tissue, the computing system comprising:
   at least one memory device;
   at least one processor; and
   at least one physical computer readable medium coupled to the at least one memory device, the at least one physical computer readable medium comprising computer executable instructions that when executed by the at least one processor are configured to:
      propagate one or more RF signals into the skin tissue, where the one or more RF signals are configured to penetrate multiple layers of the skin tissue and are in a frequency range of 30 GHz-10 THz;
      receive one or more reflected RF signals from the multiple layers of the skin tissue;
      record a digital state of each of the one or more reflected RF signals;
      construct a digital image of the skin tissue based on the digital state of each of the one or more reflected RF signals; and
      determine an authentication state based on a comparison of the digital image and a prerecorded digital image of the skin tissue.

18. The computing system of claim 17, further comprising a traveling wave antenna through which the one or more RF signals are propagated into the skin tissue using the traveling wave antenna.

19. The computing system of claim 18, further comprising a plurality of RF detectors through which the one or more reflected RF signals are received.

20. The apparatus of claim 19, where the plurality of RF detectors each comprise at least one detector antenna configured to support a same polarization as the traveling wave antenna.

* * * * *